United States Patent [19]
Liddell et al.

[11] Patent Number: 5,798,440
[45] Date of Patent: Aug. 25, 1998

US005798440A

[54] INCREASING THE PARTICLE SIZE OF POLYMERS

[75] Inventors: John Macdonald Liddell, Stockton on Tees; Neil George, Ingleby Barwick, both of England

[73] Assignee: Zeneca Limited, London, England

[21] Appl. No.: 374,662

[22] PCT Filed: Jul. 13, 1993

[86] PCT No.: PCT/GB93/01465

§ 371 Date: Jan. 24, 1995

§ 102(e) Date: Jan. 24, 1995

[87] PCT Pub. No.: WO94/02622

PCT Pub. Date: Feb. 3, 1994

[30] Foreign Application Priority Data

Jul. 24, 1992 [GB] United Kingdom ............. 9215791

[51] Int. Cl.$^6$ ................. C08F 6/18; C12P 7/64
[52] U.S. Cl. ............ 528/499; 528/361; 528/499; 528/500; 528/501; 528/502; 528/503; 435/135; 435/136

[58] Field of Search .............. 528/361, 499, 528/500, 501, 502, 503; 435/135, 146

[56] References Cited

U.S. PATENT DOCUMENTS 5,213,976  5/1993  Blauhut et al. ............ 435/135

FOREIGN PATENT DOCUMENTS 46335   2/1982  European Pat. Off. .
479043  4/1992  European Pat. Off. .

*Primary Examiner*—Samuel A. Acquah
*Attorney, Agent, or Firm*—Cushman Carby & Cushman Intellectual Property Group of Pillsbury Madison & Sutro LLP

[57] ABSTRACT

Polyester particles in suspension in a liquid can be agglomerated below their melting points and the agglomerated particles are more easily filtered.

15 Claims, No Drawings

INCREASING THE PARTICLE SIZE OF POLYMERS

THIS INVENTION relates to increasing the particle size of polymers.

In the production of polyester polymers especially those which are microbially produced the particle sizes of the polymers may be too small for convenient handling; for example in the course of production processes it may be necessary to separate such particles from aqueous liquid media. Such separations are more difficult if the particles are small than if they are large.

Surprisingly we have found that polyesters, especially those which are microbially produced, for example polymers and copolymers of hydroxyalkanoic acids especially polymers and copolymers of hydroxybutyric acid are capable of surprisingly rapid agglomeration at temperatures substantially below their peak melting points when in suspension in a liquid medium producing particles well suited to solid liquid separation with little molecular weight loss.

This invention comprises a process in which polyester particles, in suspension in a liquid medium in which if such medium comprises matter derived from microbial cells the said matter other than polyester has been at least partly chemically degraded, are agglomerated by maintaining the suspension at a temperature in excess of 80° C. and preferably in excess of 90° C. for example in excess of 100° C. and preferably 30° to 80° C. and more preferably 40° to 70° C. below the peak melting point of the polyester as determined by differential scanning calorimetry for a time sufficient to cause substantial agglomeration.

Suitable temperatures in the case of polymers of hydroxybutyric acid, for example copolymers of hydroxybutyric and hydroxyvaleric acid containing up to 25%, for example 5 to 20% of hydroxyvaleric acid residues, the balance being substantially all hydroxybutyric acid residues, are in the range 120° to 160° C. In general a considerable amount of agglomeration can be achieved with such materials in about 1 minute at 130° C. The large particles formed are agglomerates of the fine particles of the original suspension. The fine particles, in the case of microbially produced polymers, are usually <1 μm in diameter (as assessed by the diameter of a sphere of equivalent volume). The process in this case, especially in the case of polymers of hydroxybutyric acid and copolymers thereof with hydroxyvaleric acid, enables the production of a fused network of polymer strands resulting in a highly porous, mechanically strong agglomerate with excellent filtration and washing characteristics. Suitably, the agglomerates produced have a weight average diameter of at least 50 μm and preferably 100 to 1000 μm, for example 200 to 500 μm. They suitably have a high porosity for example 0.7 to 0.8 and preferably at least 0.6. Relative to non-agglomerated particles the filtration rate (based on the specific cake resistance) is increased by 100 to 10,000 times. Agglomeration may be achieved with minimal influence on molecular weight. At 30 minutes residence time at 130° C. <30% reduction is obtained, and at 1 minute the loss is undetectable.

It will be appreciated that it is necessary where the particles are derived from microbially produced polyester that the residual microbial material surrounding the particles should be at least sufficiently degraded to permit the polyester particles to come into contact with one another in the liquid medium.

We have surprisingly found that an increase in particle sizes may still be obtained despite the presence of soluble microbial components and degradation products. It may be desirable, especially if the particles initially recovered are contaminated with microbial matter or degradation products thereof to resuspend them in a second liquid medium and/or further treat them for example with a second liquid medium in which further processing for example chemical treatment (which may be treatment with a bleach for example hydrogen peroxide) may take place and to recover the particles from the new liquid medium. The process of increasing the particle size may take place at any point in the process. Such a step could take place in the presence of a liquid medium which is substantially free from contaminants and which contains substantially only materials which are desired in the final polymer or which are readily separable therefrom with the liquid.

The particle sizes are suitably increased by agitation for example in turbulent flow such as a heated stirred tank pressure vessel at a temperature at least 30° C. and more preferably at least 40° C. and preferably at most 80° C. and more preferably at most 70° C. below the melting point of the polyester as determined by the peak melting point as determined by differential thermal scanning calorimetry.

The process may be carried out by the direct injection of steam at a suitable temperature and pressure into a flowing stream of the suspension. This has the advantage that the suspension can be agglomerated continuously. However, it is surprisingly found to be possible to carry out the process in the presence of moving parts for example stirrers.

The liquid medium preferably comprises water as this is cheap and non-polluting and is very effective.

We have found that the process may be carried out with a solids concentration of up to 200 grams per liter and preferably 40 to 130 grams per liter. Above these levels there is a tendency for the medium to become substantially immobile because of the inclusion of liquid within the porous structure of the solid. The ability of the particle to be washed free from soluble cellular material is not unduly impaired by the agglomeration process.

EXAMPLE 1

Agglomeration of Polyhydroxybutyrate/polyhydroxyvalerate Copolymer Suspensions by Thermal Treatment.

A suspension of polyhydroxybutyrate/valerate polymer (8% molar hydroxyvalerate, 92% hydroxybutyrate) in water derived from Alcaligenes eutrophus and containing about 2% of cellular matter derived therefrom as an impurity was agglomerated by heating to 130° C. for 30 minutes in a stirred tank reactor. The resulting agglomerated suspension was filtered through a GFC cellulose filter (nominal pore size 1.5 micron) in a pressure filter at about $2.5 \times 10^4$ pascals pressure.

Comparative filtration data is shown for the suspension before and after the thermal agglomeration treatment in Table 1 together with data on the particle size and colour of the washed melt processed polymer.

TABLE 1

| | Weight Average Size[1] (micron) | Relative Filtration Rate[2] | Polymer Yellowness[3] (D1925-70 yellowness units) | Weight Av mol weight (K) |
|---|---|---|---|---|
| Before thermal agglomeration | 72 | 1 | 47 (±5) | 377 |

TABLE 1-continued

| | Weight Average Size[1] (micron) | Relative Filtration Rate[2] | Polymer Yellowness[3] (D1925-70 yellowness units) | Weight Av mol weight (K) |
|---|---|---|---|---|
| After thermal agglomeration (130° C., 30 minutes) | 346 | 1000 | 46 (±5) | 302 |

[1]As determined by a Malvern laser sizer
[2]The relative filtration rate is based on specific cake resistance.
[3]Centrifuged, washed by resuspension and re centrifugated in the non-agglomerated case. Filtered and washed on the filter bed only in the agglomerated case.

EXAMPLE 2

Agglomeration in the Presence of High Concentrations of Cellular Debris

A suspension of PHB/V (copolymer of hydroxybutyric and hydroxyvaleric acid) (12% molar hydroxyvalerate, 88% hydroxybutyrate) in water derived from Alkaligenes eutrophus containing 5% soluble matter derived therefrom as an impurity, was agglomerated by heating for 2 minutes in a stirred tank reactor at 126° C. The resulting agglomerated suspension was filtered through a 50 μm filter cloth in a pressure filter at 7000 Pa. The suspension was washed and analysed as above.

TABLE 2

| | Weight Average Size[1] (micron) | Relative Filtration Rate[2] | Polymer Yellowness[3] (D1925.70 yellowness units) |
|---|---|---|---|
| Before thermal agglomeration | 1.0 | 1 | 45 |
| After thermal agglomeration | 300 | 2500 | 54 |

EXAMPLE 3

Continuous Thermal Agglomeration by Direct Steam Injection

A suspension of PHB/V (8% hydroxyvalerate) in water derived from Alcaligenes Eutrophus containing 0.13% w/w soluble matter derived therefrom as an impurity, was continuous thermally agglomerated within a flowing suspension by direct steam injection. The temperature was set at 125° C., the residence time was 1 minute and turbulent conditions was maintained to achieve the following characteristics.

TABLE 3

| | Weight Average Size[1] (micron) | Relative Filtration Rate[2] | Polymer Yellowness[3] (D1925-70 yellowness units) | Weight Av mol weight (K) |
|---|---|---|---|---|
| Before thermal agglomeration | 21.4 | 1 | 41 | 523 |
| After thermal agglomeration | 250 | 2500 | 34 | 578 |

It will be seen that an important process improvement is obtained and the yellowness test indicates the substantially complete removal of impurities in all cases. If desired, the polymer may be re-suspended and filtered or the filter bed may be further washed to remove further cellular matter if desired. Less intensive solid/liquid separation techniques for example pressure filtration, decanter centrifuges produced results comparable to high g force centrifugal separation on non-agglomerated particles.

Each polymer sample was dried and melt processed at 170° C. for 4 minutes and the polymer colour measured in terms of yellowness index to ASTM D1925-70. No detrimental effect of polymer colour was apparent comparing the technique of washing and centrifugation with the approach of thermal agglomeration, filtration and washing.

We claim:

1. A process in which polyester particles in suspension in a liquid medium agglomerated by maintaining the suspension at a temperature in excess of 100° C. and 30° to 80° C. below the peak melting point of the polyester as determined by differential scanning calorimetry for a time sufficient to cause substantial agglomeration, the agglomeration being carried out in the substantial absence or any solvent.

2. A process as claimed in claim 1 in which the polyester is microbially produced.

3. A process as claimed in claim 1 or 2 in which the polyester is a copolymer of hydroxybutyric acid and hydroxyvaleric acid containing up to 25% of hydroxyvaleric acid residues, the balance being substantially all hydroxybutyric acid residues.

4. A process as claimed in claim 3 which is carried out at a temperature of 120° to 160° C.

5. A process as claimed in claim 1 in which particles of which substantially all are smaller in diameter than 1 μm are agglomerated to produce agglomerates of weight average diameter of at least 50 μm.

6. A process as claimed in claim 1 in which the aggregates have a porosity greater than 0.7.

7. A process as claimed in claim 1 which is carried out under turbulent conditions.

8. A process as claimed in claim 7 in which the process is carried out by direct injection of steam into a flowing stream of the suspension of while stirring the suspension.

9. A process as claimed in claim 1 in which the liquid medium comprises water.

10. A process as claimed in claim 1 in which the agglomerated particles are separated from the liquid medium by filtration.

11. A process as claimed in claim 10 in which the separated agglomerated particles are further washed by resuspending them in a medium water chemically treated while resuspended, and the particles then recovered.

12. A process as claimed in claim 1 in which the medium comprises matter from microbial cells and said matter other than polyester is at least partly chemically degraded.

13. A process as claimed in claim 1 wherein the suspension is maintained at a temperature in excess of 100° C.

14. A process as claimed in claim 13 wherein the temperature is 40° to 70° C. below the peak melting point of the polyester.

15. The process of claim 1 wherein the polyester particles are microbially produced and residual microbial material surrounding said particles is at least partly degraded before agglomerating.

* * * * *